United States Patent [19]

Dransfeld et al.

[11] Patent Number: 5,212,987

[45] Date of Patent: May 25, 1993

[54] ACOUSTIC SCREEN SCAN MICROSCOPE FOR THE EXAMINATION OF AN OBJECT IN THE SHORT-RANGE FIELD OF A RESONANT ACOUSTIC OSCILLATOR

[75] Inventors: Klaus Dransfeld, Ermatingen, Switzerland; Ulrich Fischer, Wetzlar, Fed. Rep. of Germany; Peter Guethner, Konstanz, Fed. Rep. of Germany; Knut Heitmann, Wetzlar, Fed. Rep. of Germany

[73] Assignee: Hommelwerke GmbH, Schwenningen, Fed. Rep. of Germany

[21] Appl. No.: 794,610

[22] Filed: Nov. 15, 1991

Related U.S. Application Data

[63] Continuation of Ser. No. 466,291, Apr. 6, 1990, abandoned.

[30] Foreign Application Priority Data

Jun. 16, 1988 [DE] Fed. Rep. of Germany ....... 3820518

[51] Int. Cl.$^5$ ............................ G01B 5/28; G01B 7/28; G01B 21/20
[52] U.S. Cl. ........................................ 73/579; 73/635; 73/105
[58] Field of Search ................. 73/643, 644, 632, 651, 73/584, 579, 105

[56] References Cited

U.S. PATENT DOCUMENTS

| | | | |
|---|---|---|---|
| 3,427,063 | 10/1969 | Branson ............................. | 73/67.1 |
| 4,294,121 | 10/1981 | Inoue ................................. | 73/662 |
| 4,473,822 | 9/1984 | Schiffl ................................. | 340/674 |
| 4,577,505 | 3/1986 | Jestrich et al. ..................... | 73/629 |
| 4,646,573 | 3/1987 | Stoll .................................... | 73/606 |
| 4,751,686 | 6/1988 | Uchino et al. ..................... | 367/7 |
| 5,077,695 | 12/1991 | Khuri-Yakab et al. ............ | 73/642 |

FOREIGN PATENT DOCUMENTS

| | | |
|---|---|---|
| 0198944 | 10/1986 | European Pat. Off. . |
| 0112401 | 4/1987 | European Pat. Off. . |
| 0223918 | 6/1987 | European Pat. Off. . |
| 3723933 | 2/1989 | Fed. Rep. of Germany . |
| 2114745 | 8/1983 | United Kingdom . |

OTHER PUBLICATIONS

Thaer et al., "The Elsam Acoustic Microscope," Leitz Scientific and Technical Inf., vol. VIII, No. 314, May 1987 pp. 61–67.

Zieniuk et al., "Ultrasonic Pin Scanning Microscope A New Approach to Ultrasonic Microscopy," IEEE Ultrasonics Symposium 1986, pp. 1037–1039.

Quartz Crystal Resonator DS-26, ETA S. A. CH-2540 Grenchen.

Quartz Crystal Resonator CX-MV, ETA S. A. CH-2540 Grenchen.

Dinger, "A Miniature Quartz Resonator Vibrating at 1 MHz," Proc. 35th Ann. Freq. Control Symposium, USAERADCOM, May 1981, pp. 144–148.

DiStefano et al., "Acoustic Contour Mapping," IBM Technical Disclosure Bulletin, vol. 25, No. 10, Mar. 1983, pp. 5103–5108.

Bertoni, "Ray-Optical Evaluation of V(z) in the Reflection Acoustic Microscope," IEEE Transactions on Sonics and Ultrasonics, vol. SU-31, No. 2, Mar. 1984, pp. 105–116.

*Primary Examiner*—Hezron E. Williams
*Assistant Examiner*—Rose M. Finley
*Attorney, Agent, or Firm*—Foley & Lardner

[57] ABSTRACT

An acoustic scanning microscope uses damping of a resonant acoustic oscillator and an acoustic near-field effect. In a preferred embodiment, a 32 KHz tuning fork serving as an acoustic oscillator with a 50 nm point achieves a vertical resolution of 5 nm and a horizontal resolution of 50 nm in the case of a minimum distance of approximately 50 nm. Frequency or amplitude variation of the resonant acoustic oscillator can be used. The acoustic near-field effect is dependent on the coupling medium, e.g., air, and the pressure, e.g., normal pressure.

15 Claims, 3 Drawing Sheets

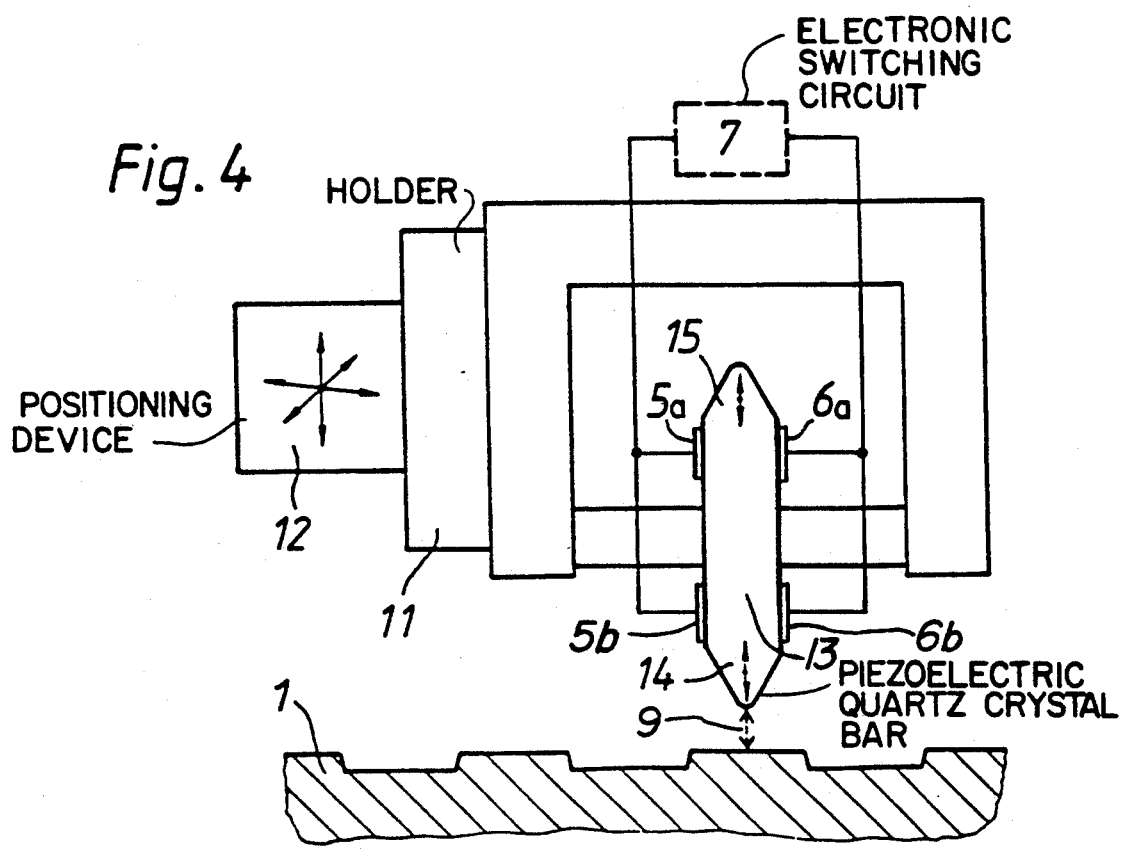

ACOUSTIC SCREEN SCAN MICROSCOPE FOR THE EXAMINATION OF AN OBJECT IN THE SHORT-RANGE FIELD OF A RESONANT ACOUSTIC OSCILLATOR

This application is a continuation of application Ser. No. 07/466,291, filed Apr. 6, 1990, now abandoned.

BACKGROUND OF THE INVENTION

The invention is directed to an acoustic scanning microscope which utilizes reciprocal effects in the acoustic near-field of an object. In this context, the expression "near-field" signifies that the size of the radiation source and its distance from the object are approximately the same and significantly smaller than the wavelength of the radiation used. An important feature in a near-field arrangement is that the resolution is no longer classically limited by the wavelength of the radiation used, but instead can be much smaller, and is determined by the size and distance of the radiation source. This is known, e.g., for an optical near-field scanning microscope discussed in European Published Patent Specification EP-B2 112,401.

An acoustic scanning microscope which undershoots the classical resolution limit and achieves a resolution of approximately one tenth of the sound wavelength is discussed by J. K. Zieniuk and A. Latuszek in IEEE Ultrasonics Symposium 1986 at pages 1037–1039.

Ultrasonic waves of approximately 3 MHz are transmitted through the object (coupled via a fluid coupling medium to a sound waveguide held at a short distance above the object) and fed from the latter to a transducer serving as a detector. A conical frustum shape of the sound waveguide, whose area of coverage of approximately 20 µm in diameter is distinctly smaller than the sound wavelength used (approximately 0.5 mm), faces the object. The size of the surface area covered determines the achievable resolution.

Such a microscope is also discussed in U.S. Pat. No. 4,646,573.

A transmission arrangement of this type is basically suitable only for a narrow class of objects.

A reflex arrangement with a conical frustum instead of an acoustic lens is possible in theory. However, in such an arrangement there occurs high power losses, the necessity for pulse operation, and substantial disturbances due to various reflexes, all of which have occurred to a lesser extent in the classical acoustic microscope (see A. Thaer, M. Hoppe, W. J. Patzelt, Leitz Mitt. Wiss. Techn. VIII (1982), pages 61–67).

A power microscope is discussed in European Published patent Specification EP-A2 223,918. This microscope acquires a topographic image of an object by bringing up a point so close to the object that the electron clouds of the atoms in the point and in the object overlap, so that interatomic forces occur. This distance is less than 1 nm. The point is attached to a bar spring, and forces are detected through the influence of the spring deflection on a scanning tunnelling microscope observing the spring. In this regard, it is proposed to cause the bar spring to oscillate at its natural frequency of 2 KHz and at an amplitude smaller than 1 nm in the z direction. This introduces a carrier frequency response which reduces the effects of errors. With this power microscope it is especially advantageous to locate the object and the detection system in an ultra high vacuum (approximately $10^{-8}$ Pa).

German Publication DE 3,723,933 A1 (which was not published prior to development of the instant invention) discusses a contact detector for contact surfaces in the region of about one square micrometer and contact forces in the region of less than one millinewton. In this device, a bar-shaped resonator with a pointed probe is excited to have natural mechanical oscillations in the longitudinal direction and a contact signal appears if during the approach of the probe to the measurement surface the amplitude falls by, e.g., a decibel. Frequency variations can also be detected. It is possible for a surface to be scanned and the amplitude to be constantly regulated in the process. Separate pairs of electrodes are provided for exciting and detecting oscillations of the resonator. Detuning is achieved through direct mechanical contact without a coupling medium, as occurs in the case of hardness tests. Characteristics of the acoustic field, including the acoustic near-field, are not discussed.

SUMMARY OF THE INVENTION

It is an object of the present invention to provide an acoustic scanning microscope whose resolution is distinctly increased absolutely and relative to the sound wavelength over the prior art, and whose resolution lies in the submicron range. It is an object of the invention to be functionally independent of transmission and reflection characteristics of the object, and to operate without a fluid coupling medium.

These objects are achieved by providing an acoustic scanning microscope with the features described below. It has been discovered that the known near-field effects for radiation sources of the various physical electromagnetic waves, including light, also occur in an equivalent fashion in the case of acoustic fields. Differences do exist in that different multipoles are involved, i.e., an acoustic monopole can emit soundwaves, but at least one dipole is necessary for electromagnetic waves.

The advantageous features relating to resolving power which are known from optical scanning microscopy can therefore be transferred to an acoustic scanning microscope, taking into account the different wavelengths.

Resonant acoustic oscillators are produced, e.g., in the horological industry in the form of miniaturized quartz crystals. Methods for excitation and measurement of the state of oscillation are also known from this application.

In accordance with the invention, the near-field effects between such a resonant acoustic oscillator and an object are used for scanning microscopy.

In comparison with the conventional high-resolution acoustic scanning microscope (for example, those of J. K. Zieniuk and A. Latuszek, or U.S. Pat. No. 4,646,573), the invention has the advantage that there is no need for any separate receiving device which must detect a low radiation intensity influenced by the object and discriminate between the latter and strong influences of high intensity emitted radiation. In the invention, the transmitter is directly influenced by the object, and reception of emitted soundwaves which have made contact with the object does not take place. The resonant excitation of the oscillator takes place in continuous operation. It is guided over the object to be examined in the region of the acoustic near-field.

BRIEF DESCRIPTION OF THE DRAWINGS

The invention is described in more detail below in connection with illustrative embodiments, which are shown in the drawings, wherein:

FIG. 3 illustrates an arrangement having a tuning fork oscillator, one corner of which acts as a probe point and oscillates obliquely to the object, an illustrative embodiment of the electrode arrangement is also illustrated;

FIG. 4 illustrates a diagram of an acoustic scanning microscope which includes a bar oscillator having one end constructed as a probe point.

DETAILED DESCRIPTION OF THE PREFERRED EMBODIMENTS

Figure 1:
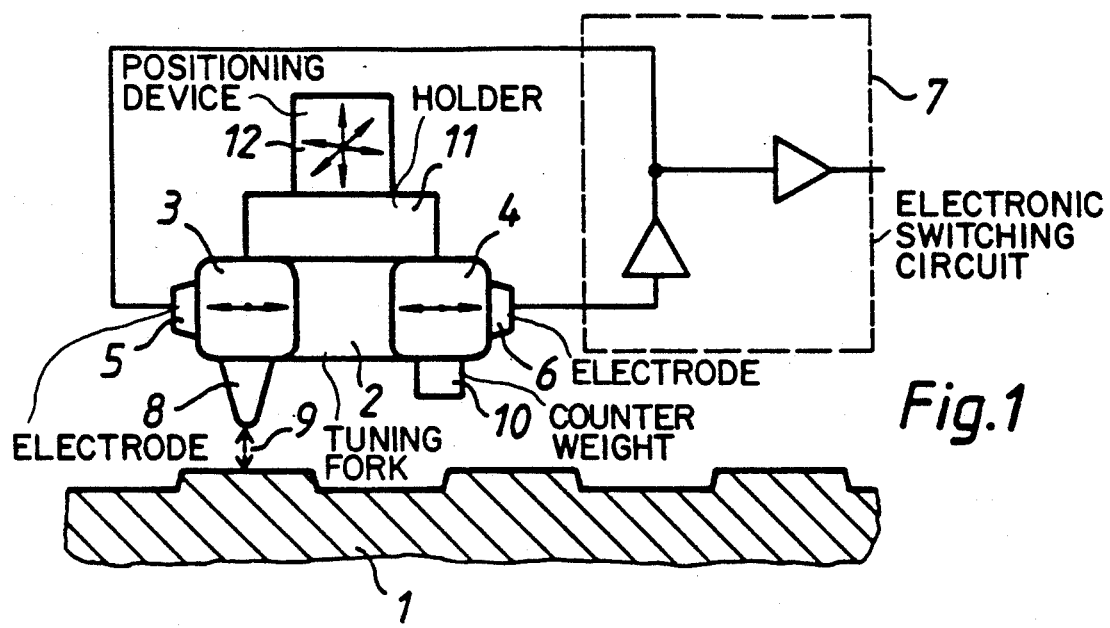
FIG. 1 illustrates a diagram of an acoustic scanning microscope with a tuning fork quartz crystal as an oscillator, which oscillates parallel to the object.

A section through an object 1 having a structure is shown in FIG. 1. Represented in the diagram parallel to the surface of the object 1 at a suitable distance, are a tuning fork 2 with ends 3 and 4 and two electrodes 5 and 6 for excitation. The ends 3 and 4 of the tuning fork 2 oscillate parallel to the surface of the object 1 at the resonant frequency of the tuning fork 2.

The tuning fork 2 consists, for example, of a piezoelectric quartz crystal, excitation and measurement taking place through the piezoelectric effect via the two electrodes 5 and 6. For this purpose, there is connected to the latter an electronic switching circuit 7, which excites the tuning fork 2 to its natural resonance by electronic feedback, and also measures the damping of the tuning fork 2.

Attached as a probe to one end 3 of the tuning fork 2 is a fine point 8 which reaches to within a small distance 9 from the object 1. A counterweight 10 for stabilizing the resonant response of the tuning fork 2 can be provided at the other end 4.

The tuning fork 2 with the point 8 is attached via a holder 11 to a three-dimensional positioning device 12. The latter makes it possible to bring the point 8 into the measuring distance from the object 1, and to scan the latter using a raster-like motion. Suitable designs for the positioning device 12 are known in scanning microscopy, and especially in scanning tunnelling microscopy. These include piezodrives which are subdivided into coarse and fine drives with a precision which is matched to the resolution of the acoustic scanning microscope.

Figure 2:
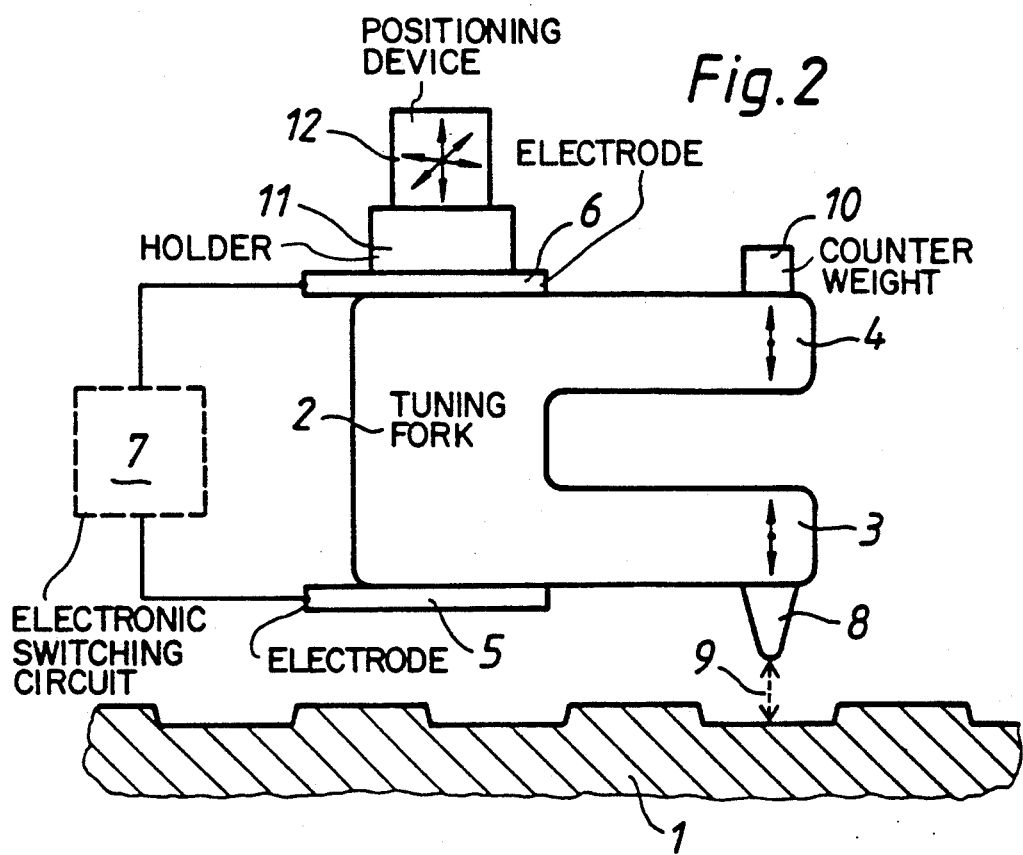
FIG. 2 is similar to FIG. 1 except that the direction of oscillation is perpendicular to the object.

FIG. 2 illustrates an arrangement of the same elements for application with the direction of oscillation perpendicular to the object 1. For this configuration, the tuning fork 2 is rotated in place perpendicular to the object 1, and point 8 at the end 3 is similarly rotated.

In FIG. 3, the tuning fork 2 and also the direction of oscillation are inclined obliquely with respect to the surface of the object 1. As illustrated, a corner of the tuning fork 2 can be used directly as point 8a, without any additional structure. If desired, the design of the tuning fork 2 can be optimized to include integrated point 8a.

Tuning forks such as those employed in quartz crystal resonators DS-26 of the firm of ETA S.A. CH-2540 Grenchen, are suitable for the arrangements of FIGS. 1 to 3. In these tuning forks, the two electrodes are each subdivided into a plurality of subphases 5a, 5b, 5c, 5d; 6a, 6b, 6c, 6d, as is represented diagrammatically in FIG. 3, and are distributed on the two arms of the tuning fork, because this results in more effective coupling between electrical and mechanical-acoustic oscillation than is the case with the arrangement of FIG. 1. The resonant frequency lies at 32 KHz, and thus the sound wavelength in air is 1 cm. Typical dimensions of the ends 3 and 4 are approximately 0.1 mm. The oscillation amplitude amounts to less than 1 $\mu$m at the ends 3 and 4.

The resonator quality (quality factor) is greater than 50,000. Switching circuits 7 for exciting and measuring frequency or amplitude, and thus damping, are known for such resonators, and are commercially available.

In the arrangement of FIG. 3, without special shaping of the point 8a and with a distance 9 on the order of magnitude of 0.1 mm, the resonant frequency of the tuning fork 2 varies typically by 2 Hz per 0.1 mm change in the distance 9 at normal pressure, in air. This is described in more detail in connection with FIG. 5. In this regard, the z distance resolution already amounts to a ten thousandth of a wavelength, in round numbers.

If, in an arrangement according to FIG. 1 or 2, the point 8 is provided with a point radius of approximately 50 nm, as is customary for points for scanning tunnelling microscopes, a distance resolution of approximately 5 nm is achieved over a distance region of approximately 100 nm. If the distance 9 corresponds approximately to the point radius, then the lateral resolution is approximately 50 nm.

Apart from the use of frequency shift, amplitude variation of the resonant oscillator can also be effectively used to measure the damping of the tuning fork 2 by the near object 1. The amount of damping corresponds to the position of the point 8, which is known from the output(s) of the positioning device 12, and is processed to generate a micro-image by scanning.

As with the scanning tunnelling microscope, it is advantageous when scanning an object 1 to regulate the distance 9 of the point 8 from the object 1 in a way such that the oscillation amplitude or the resonant frequency remains constant during the scanning. The regulating signal then defines a profile of the surface of the object 1 as a function of the scanning points. In addition to height information, in this process the local elastic characteristics of the object 1 are also determined in principle.

Like other scanning microscopes, the instant acoustic near-field scanning microscope also offers the possibility of influencing the object 1 locally at the surface. In particular, acoustic surface waves can be generated locally.

In the case of an embodiment which has a fine point 8, the oscillation amplitude at the ends 3 and 4 of the tuning fork 2 is substantially larger than the working distance 9 and the resolution.

The amplitude of oscillation of the point 8 can be reduced if it is moved away from the end 3 towards the base of the tuning fork 2. However, the influencing of the tuning fork 2 by the near-field effect is also then reduced.

The amplitude can also be reduced as much as 10 nm by electronic control of the oscillation excitation. A smaller amplitude can also be achieved by exciting the tuning fork 2 with an overtone frequency.

Depending upon the application at hand, the parallel direction of oscillation according to FIG. 1 can be chosen for high distance resolution or the vertical direction of oscillation according to FIG. 2 can be chosen for high lateral resolution. In the arrangement according to FIG. 2, the mean distance 9 between point 8 and object 1 is then large in the case of an amplitude of approximately 1 μm as compared with the radius of curvature of the point 8. The near-field effect therefore acts essentially in the intervals in which the oscillation of the tuning fork 2 reaches somewhat more than 90% of the maximum deflection in the direction of the object 1. However, the required minimum distance 9 of the point 8 from the object 1 (e.g. 50 nm) at the point of reversal is too large as compared with the distance resolution achieved (e.g. 5 nm).

The risk of damage to point 8 and object is consequently slight in contradistinction to, for example, the power microscope discussed in EP-A2 223,918, in which the working distance of the point and the distance resolution both typically lie at 0.1 nm.

FIG. 4 illustrates, in diagrammatic form that the resonant acoustic oscillator employed in the invention is not restricted to a tuning fork 2.

In FIG. 4, the tuning fork is replaced with a piezoelectric quartz crystal bar 13, which is clamped-in at its center. The ends 14 and 15 oscillate in antiphase in the longitudinal direction of the bar 13. Excitation is provided by electrodes 5a and 5b and 6a and 6b. The end 14 opposite the object 1 at a distance 9 can be constructed as a point. The rest of the arrangement is similar to those of FIGS. 1 to 3. A suitable quartz crystal oscillator bar 13 is contained, e.g., in the quartz crystal resonator CX-MV of the firm of ETA S.A. CH-2540 Grenchen. A typical resonant frequency for this arrangement is 1 MHz; the sound wavelength in air therefore being approximately 0.33 mm. Such a quartz resonator is also described in R. J. Dinger, Proc. 35th Ann. Freq. Control Symposium, USAERADCOM, Ft. Monmouth, N.J., May 1981, pages 144 ff.

The mode of operation is otherwise the same as in the examples of FIGS. 1 to 3.

The quartz oscillators discussed, and also sketched in FIGS. 1 to 4, have the particular characteristic that they consist of a pair of bar or bar oscillators excited to antiphase oscillation. They are arranged in the acoustic near-field scanning microscope in a way such that only one of the bars (or bar) comes into interaction with the object 1. The result of this is that in the case of a large distance from the object 1, so long as no noticeable interaction occurs, no oscillations are transferred from the oscillator to the holder 11 (FIG. 1), because the mounting of the oscillator to the holder 11 is done at a node. However, if due to interaction with the object 1 the pair of oscillators is subjected to one-sided loading, a transfer of oscillation takes place to the holder 11. This oscillation is damped in the holder 11. This leads to an increase in the measuring sensitivity, because under these conditions the change in damping is substantially larger than that which occurs due to only the interaction of the oscillator with the object 1.

Figure 5:
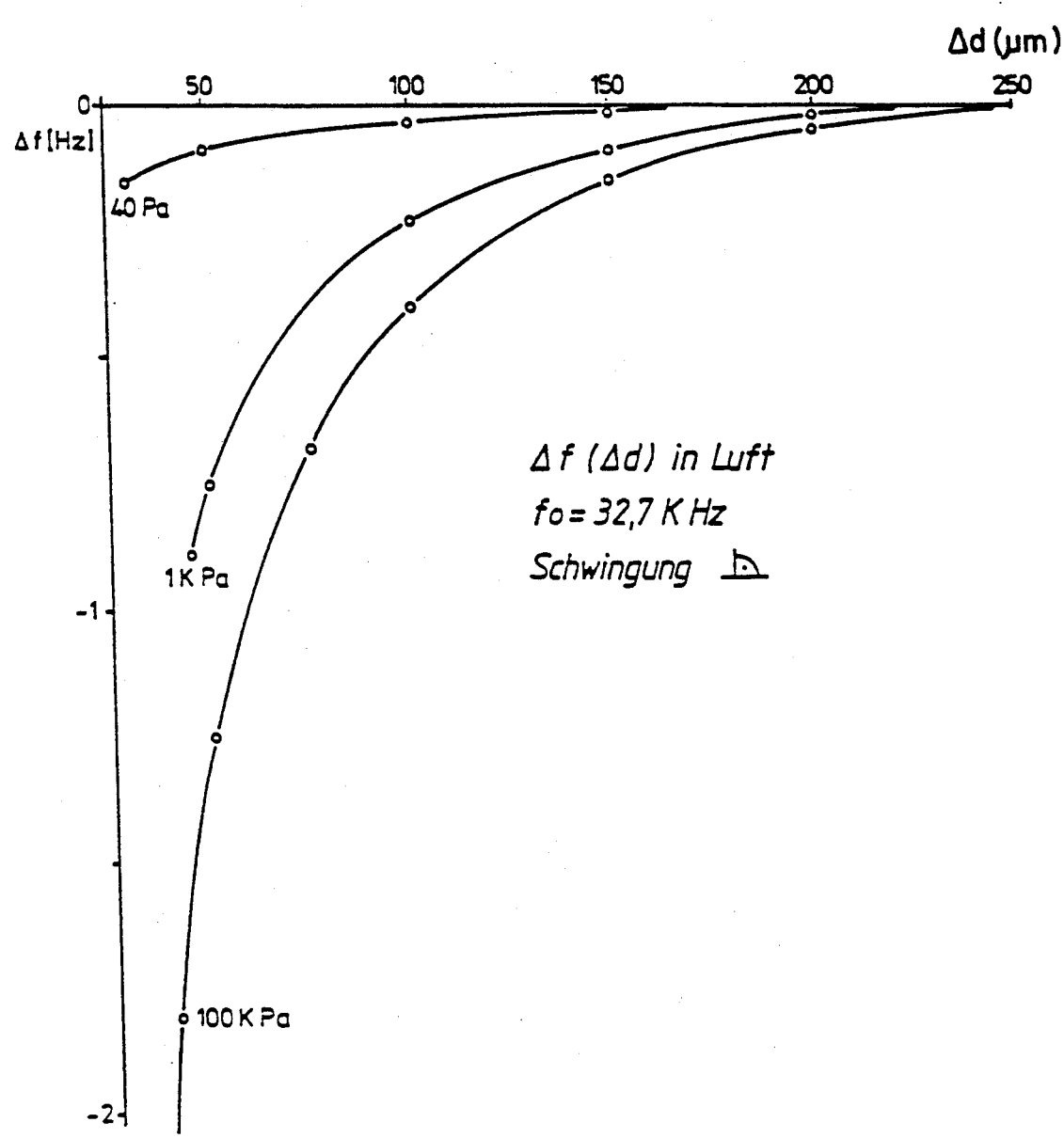
FIG. 5 an experimentally obtained diagram of the frequency shift of a tuning fork oscillator as a function of the distance from the object in the near-field region, the dependency of the effect of gas pressure being clearly apparent.

FIG. 5 illustrates a diagram of the frequency shift of the resonant frequency of the resonant acoustic resonator as a function of the distance 9 ($\Delta d$) between the tuning fork 2 and the object 1 in air.

The measured values were acquired with an arrangement in which a tuning fork 2 according to FIG. 3 (without a special tip 8 as in FIG. 2) oscillates perpendicular to a curved metal surface serving as object 1. This specified relative distance $\Delta d$ is not calibrated to contact at $\Delta d = 0$ μm.

The pressure dependency of the characteristics shows the acoustic nature of the effect, which does not exist without a coupling medium. At a vacuum of only 1.5 Pa, the frequency varies by at most 0.2 Hz over the distance region shown in the diagram for pressures of 40 Pa, 1 KPa and 100 KPa (normal pressure). At normal pressure, the frequency variation exceeds this value a hundred-fold. Apart from air, other gases, e.g., helium, are also suitable as a coupling medium. The frequency/distance characteristics also change when different gases are used in accordance with the acoustic properties.

What is claimed is:

1. An acoustic scanning microscope for examining an object, said acoustic scanning microscope comprising:
   a resonant acoustic oscillator located adjacent to, but not contacting, said object as said acoustic oscillator oscillates such that said object is in an acoustic field of said acoustic oscillator, said acoustic field being defined as a field created when a size of a radiation source and its distance from said object are approximately the same and are significantly smaller than a wavelength of acoustic radiation used; and
   means for determining the damping of said acoustic oscillator as a function of the position of said object in relation to said acoustic oscillator to generate a micro-image profile of said object.

2. An acoustic scanning microscope for examining an object, said acoustic scanning microscope comprising:
   a resonant acoustic oscillator located adjacent to, but not contacting, said object as said acoustic oscillator oscillates such that said object is in an acoustic field of said acoustic oscillator, said acoustic field being defined as a field created when a size of a radiation source and its distance from said object are approximately the same and are significantly smaller than a wavelength of acoustic radiation used; and
   means for determining the damping of said acoustic oscillator as a function of the position of said object in relation to said acoustic oscillator;
   wherein said acoustic oscillator includes a coupled pair of acoustic oscillators.

3. An acoustic scanning microscope according to claim 2, wherein said acoustic oscillator includes a tuning fork.

4. An acoustic scanning microscope according to claim 2, wherein said acoustic oscillator includes a centrally fixed bar with free ends.

5. An acoustic scanning microscope for examining an object, said acoustic scanning microscope comprising:
   a resonant acoustic oscillator located adjacent to, but not contacting, said object as said acoustic oscillator oscillates such that said object is in an acoustic field of said acoustic oscillator, said acoustic field being defined as a field created when a size of a radiation source and its distance from said object are approximately the same and are significantly smaller than a wavelength of acoustic radiation used; and means for determining the damping of said acoustic oscillator as a function of the position of said object in relation to said acoustic oscillator;

wherein said acoustic oscillator oscillates perpendicular to the surface of said object.

6. An acoustic scanning microscope according to claim 1, wherein said acoustic oscillator oscillates perpendicular to the surface of said object.

7. An acoustic scanning microscope for examining an object, said acoustic scanning microscope comprising:

a resonant acoustic oscillator located adjacent to, but not contacting, said object as said acoustic oscillator oscillates such that said object is in an acoustic field of said acoustic oscillator, said acoustic field being defined as a field created when a size of a radiation source and its distance from said object are approximately the same and are significantly smaller than a wavelength of acoustic radiation used; and means for determining the damping of said acoustic oscillator as a function of the position of said object in relation to said acoustic oscillator;

wherein said acoustic oscillator is shaped and arranged with respect to said object such that a specific small portion of said acoustic oscillator with a high oscillation amplitude comes into the closest proximity with said object to serve as a probe point.

8. An acoustic scanning microscope according to claim 1, wherein a gas is introduced as a coupling medium between said acoustic oscillator and said object.

9. An acoustic scanning microscope according to claim 1, wherein a frequency variation of said acoustic oscillator oscillating at natural resonance is utilized as a measure of said damping.

10. An acoustic scanning microscope according to claim 9, wherein amplitude variation of said acoustic oscillator oscillating at natural resonance is utilized as a measure of said damping.

11. An acoustic scanning microscope for examining an object, said acoustic scanning microscope comprising:

a resonant acoustic oscillator located adjacent to, but not contacting, said object as said acoustic oscillator oscillates such that said object is in an acoustic field of said acoustic oscillator, said acoustic field being defined as a field created when a size of a radiation source and its distance from said object are approximately the same and are significantly smaller than a wavelength of acoustic radiation used; and means for determining the damping of said acoustic oscillator as a function of the position of said object in relation to said acoustic oscillator;

wherein during scanning of said object a distance between said acoustic oscillator and said object is regulated such that said damping of said acoustic oscillator is compensated to a constant extent.

12. An acoustic scanning microscope for examining an object, said acoustic scanning microscope comprising:

a resonant acoustic oscillator located adjacent to, but not contacting, said object as said acoustic oscillator oscillates such that said object is in an acoustic field of said acoustic oscillator, said acoustic field being defined as a field created when a size of a radiation source and its distance from said object are approximately the same and are significantly smaller than a wavelength of acoustic radiation used; and means for determining the damping of said acoustic oscillator as a function of the position of said object in relation to said acoustic oscillator;

wherein said acoustic oscillator has a resonator quality greater than one thousand.

13. An acoustic scanning microscope according to claim 1, wherein said acoustic oscillator includes piezoelectric material.

14. An acoustic scanning microscope for examining an object, said acoustic scanning microscope comprising:

a resonant acoustic oscillator located adjacent to, but not contacting, said object as said acoustic oscillator oscillates such that said object is in an acoustic field of said acoustic oscillator, said acoustic field being defined as a field created when a size of a radiation source and its distance from said object are approximately the same and are significantly smaller than a wavelength of acoustic radiation used; and means for determining the damping of said acoustic oscillator as a function of the position of said object in relation to said acoustic oscillator;

wherein said acoustic oscillator includes piezoelectric material and wherein said acoustic oscillator is provided with two structured electrodes and is connected to an electronic switching circuit which effects excitation of said acoustic oscillator at its natural resonance by electronic feedback.

15. An acoustic scanning microscope for examining an object, said acoustic scanning microscope comprising:

a resonant acoustic oscillator located adjacent to, but not contacting, said object as said acoustic oscillator oscillates such that said object is in an acoustic field of said acoustic oscillator, said acoustic field being defined as a field created when a size of a radiation source and its distance from said object are approximately the same and are significantly smaller than a wavelength of acoustic radiation used; and means for determining the damping of said acoustic oscillator as a function of the position of said object in relation to said acoustic oscillator;

wherein said acoustic oscillator includes a coupled pair of oscillators oscillating in antiphase, which is mounted at a nodal point of coupled oscillation such that no oscillations are transferred to a mounting as long as no interaction with said object occurs.

* * * * *